United States Patent
Kerrien et al.

(10) Patent No.: US 6,854,884 B2
(45) Date of Patent: Feb. 15, 2005

(54) SYSTEM AND METHOD OF CALIBRATING AN IMAGE SYSTEM AND STORAGE MEDIUM

(75) Inventors: Erwan Kerrien, Nancy (FR); Eric Maurincomme, Chevreuse (FR); Regis Vaillant, Villebon sur Yvette (FR); Laurent Launay, St. Remy les Chevreuse (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 282 days.

(21) Appl. No.: 10/116,622

(22) Filed: Apr. 4, 2002

(65) Prior Publication Data

US 2002/0163996 A1 Nov. 7, 2002

(30) Foreign Application Priority Data

Apr. 27, 2001 (FR) .............................. 01 05754

(51) Int. Cl.$^7$ .............................................. G01D 18/00
(52) U.S. Cl. ..................................................... 378/207
(58) Field of Search ........................ 378/62, 98.2, 162, 378/164, 207

(56) References Cited

U.S. PATENT DOCUMENTS

| | | | | |
|---|---|---|---|---|
| 4,736,399 A | * | 4/1988 | Okazaki ..................... 378/98.2 |
| 4,945,223 A | * | 7/1990 | Beauzamy ............. 250/214 VT |
| 5,235,528 A | * | 8/1993 | Silver et al. ..................... 378/7 |
| 5,263,074 A | * | 11/1993 | Sakamoto .................. 378/98.2 |
| 5,336,880 A | * | 8/1994 | Leclerc et al. ......... 250/214 VT |
| 5,442,674 A | * | 8/1995 | Picard et al. .................. 378/20 |
| 5,526,442 A | * | 6/1996 | Baba et al. .................. 378/132 |
| 6,018,565 A | * | 1/2000 | Ergun et al. ................... 378/95 |
| 6,379,043 B1 | * | 4/2002 | Zylka et al. ................. 378/207 |
| 6,585,412 B2 | * | 7/2003 | Mitschke .................... 378/207 |

FOREIGN PATENT DOCUMENTS

WO 0058717 10/2000

OTHER PUBLICATIONS

Kerrien et al., Machine precision assessment for 3D/2D digital subtracted angiography images registration, SPIE Conf. on Image Processing, San Diego, CA, Feb. 1998; vol. 3388, pp. 39–49.

Kerrien, Outils d'imagerie multimodalite pour la neuroradiologie interventionnelle, thesis (http://www.loria.fr/–kerrien/these/these/pdf); Loria, France, Jan 2001.

* cited by examiner

*Primary Examiner*—Edward J. Glick
*Assistant Examiner*—Allen C. Ho
(74) *Attorney, Agent, or Firm*—Jay L. Chaskin; Cantor Colburn LLP (57) ABSTRACT

A system and method of calibrating an imaging system, in which intrinsic parameters relating to the various types of image which can be taken are calibrated in predetermined angular positions of an emitter of radiation, and of a receiver of the radiation. The intrinsic parameters are estimated using a two-dimensional phantom in order to establish a distortion field for a particular angulation, the distortion field for any angulation being calculated by polynomial interpolation of the distortion fields, each established for a control point, a control point being defined by a particular angulation for each axis of rotation of the imaging system, having to be subject to calibration.

35 Claims, 3 Drawing Sheets

SYSTEM AND METHOD OF CALIBRATING AN IMAGE SYSTEM AND STORAGE MEDIUM

CROSS REFERENCE TO RELATED APPLICATIONS

This application claims the benefit of a priority under 35 USC 119 to French Patent Application No. 0105754 filed Apr. 27, 2001, the entire contents of which are hereby incorporated by reference.

BACKGROUND OF THE INVENTION

The present invention relates to the field of calibrating an image processing sequence in order to correct distortions, in particular in two-dimensional radiological images, for example in the field of radiology.

A radiology system is known to comprise a means for emitting an X-ray beam or an X-ray unit such as an X-ray tube and a means for receiving the beam, such as a solid-state detector or a scintillator and a video camera, for example of the CCD type. The means for emitting an X-ray beam and the means for receiving are generally supported by a mobile system with one or more axes, to take pictures at various angles of incidence. The means for receiving is connected to means for image processing to generate three-dimensional images from a series of two-dimensional images taken by the means for receiving. Correspondence is desirable between a three-dimensional image and a two-dimensional image taken during a step in which the patient undergoes a particular action, such as placing a catheter in the field of angiography, in order to be able to follow the movement of the catheter in the two-dimensional image but also in the three-dimensional image. The radiology system is calibrated on commissioning and then at regular intervals, in order to take into account the imperfections for the various elements of the radiology system, such as the deformation of the supports of the means for emitting an X-ray beam and the means for receiving sensor inaccuracies, receiver defects, etc. In certain configurations, the system is calibrated at short intervals, for example a week, hence immobilization of the system and a considerable implementation cost.

BRIEF DESCRIPTION OF THE INVENTION

An embodiment of the present invention provides, in particular, a system and method and storage medium for calibration to improve the accuracy of the images obtained for all the distortion configurations and of the intrinsic parameters of the conical geometry of the system.

An embodiment of the present invention provides, in particular, a system and method and storage medium for calibration which is economic and reduces the length of time of the maintenance calibration operations carried out regularly throughout the life of an imaging system.

The system and method and storage medium calibration, according to one aspect of the invention, is intended for an imaging system comprising means for emitting a high-energy beam; means for receiving the high-energy beam after it has passed through a member to be studied; means for controlling the means for receiving; means for supporting the member and means for editing images. Intrinsic parameters relating to the various types of image which can be taken are calibrated in a predetermined configuration of the system, the intrinsic parameters being estimated using a two-dimensional phantom in order to establish a distortion field for a particular configuration, the distortion field for any configuration being calculated by combining a plurality of distortion fields from causes assumed to be independent.

BRIEF DESCRIPTION OF THE DRAWING

A particular embodiment of the invention is illustrated by the appended drawings in which.

DETAILED DESCRIPTION OF THE INVENTION

In one embodiment of the invention, a distortion field $D_0$ due to the earth's electromagnetic field is determined from an image of the phantom taken in a central position of the imaging system along each axis of rotation, the distortion field $D_0$ being independent of the angulation. The distortion field $D_0$ will be recalculated frequently to take account of the variations in the earth's electromagnetic field. In contrast, the other distortions develop more slowly and will be able to be recalculated less frequently, for example, annually.

In one embodiment of the invention, the intrinsic parameters relating to the various types of image that can be taken are calibrated in predetermined angular positions of the means for emitting and of the means for receiving, the intrinsic parameters being estimated using a two-dimensional phantom in order to establish a distortion field for a particular angulation, the distortion field for any angulation being calculated by polynomial interpolation of the distortion fields, each one established for a control point, a control point being defined by a particular angulation for each axis of rotation of the imaging system, having to be subject to calibration.

Preferably, the control points are defined such that they completely and regularly cover the field of possible orientations of the machine in question. If rotation is possible over more than 180° around one axis, it is enough to take −90°, 0° and +90° as particular angulations, 0° being the median position with respect to the extremes.

Preferably, the interpolation function is of the biquadratic or bicubic type.

A relationship can be established between the interpolation parameters u, v and the angulation, the relationship being of the type $u(x)=ax^5+bx^3+cx$, where x is a coordinate of one point, such that the distortion field is determined as a function of the angulation, the interpolation function determines the distortion as a function of the interpolation parameters u, v. The function u(x) is of the type $u(x)=\alpha(A+\beta)x^5+\chi(A+\delta)x^3+\epsilon(A+\Phi)x$, type, where A is a dependent constant of the type of imaging system $\alpha, \beta, \chi, \delta, \epsilon$ and $\Phi$ being constants which are determined experimentally. More particularly, the function u(x) is of the type $u(x)=(A-1.5)x^5+(2.5-2A)x^3+Ax$. A can be greater than or equal to 0 and less than or equal to 15/8.

Preferably, an interpolation parameter is used for each angle defining the position of the imaging system. A will be calculated for each angle. There will be $(n+1)^2$ control points, where the minimum value of n is 2 for the biquadratic interpolation and 3 for the bicubic interpolation.

In one embodiment of the invention, a distortion field $D_I$ due to an image reversal by reversing the scanning direction of the means for receiving the high-energy beam is determined by comparing an image of the phantom, which image is turned over after being taken, with an image of the phantom taken with reverse scanning, for the scanning changes used.

In one embodiment of the invention, a distortion field $D_R$ due to a change in resolution of the means for receiving the high-energy beam is determined by comparing an image of the phantom taken at a first resolution with an image of the phantom taken at a second resolution different from the first, for the resolution changes used.

In one embodiment of the invention, a distortion field $D_M$ due to a change of the acquisition matrix of the means for receiving the high-energy beam is determined by comparing an image of the phantom taken using a first acquisition matrix with an image of the phantom taken using a second acquisition matrix different from the first, for example when changing from one acquisition matrix of 512×512 pixels to an acquisition matrix of 1024×1024 pixels, for the changes of acquisition matrix used.

In one embodiment of the invention, the two-dimensional phantom comprises a grid.

In one embodiment of the invention, a calibration is carried out on installing the imaging system. This may be a calibration of the parameters of the conical geometry and of the constant A.

Furthermore, it is possible to calibrate the extrinsic parameters relating to the position of the member with respect to the imaging system, means for receiving and the means for support, in order to determine the acquisition geometry and the distortion field whatever the position of the emitting means and of the receiving means, the extrinsic parameters being calculated using a three-dimensional phantom for predetermined positions of the emitting means. The same phantom may serve to calibrate the two types of parameters.

The predetermined positions for calculating the intrinsic parameters take into account the distance between the means for emitting and the means for receiving the resolution and the image matrix.

In one embodiment of the invention, at least three images of a phantom are taken for three different values of the distance between the means for emitting and the means for receiving.

In one embodiment of the invention, the position of the imaging system is measured by sensors.

In one embodiment of the invention, a calibration is carried out at predetermined time intervals. The invention corrects distortions in numerous types of imaging systems, especially radiology systems with two-or three-dimensional images.

Another application would simply be to obtain geometrically correct images in order to be able to carry out more reliable measurements in the two-dimensional images. This is also valid for estimating the intrinsic parameters of the conical geometry which make it possible to deduce, among other things, the magnification of the images, which helps the 2D/3D registration but which also makes it possible to change measurements made in the images (therefore given in pixels) into metric measurements (therefore in millimeters).

It is desired to estimate the distortion field present in the radiographic images, whatever the configuration of the system when taking the image. The benefit of being able to estimate this distortion field is that it is possible by virtue of this knowledge to correct the images of distortions. The radiographic images are then geometrically correct, which makes it possible to use a conical projection model in a 2D/3D registration method, but also to be able to make more reliable measurements in the 2D images.

A special method is necessary, given the large number of possible configurations of the system. The general principle of the method is to find the differential distortion with respect to a reference distortion field $D_0$. This differential distortion is mainly due to four causes taking place on changing the configuration of the system.

1) Changing the direction of camera scanning;
2) Changing the acquisition matrix;
3) Changing the size of the field of view; and
4) Changing the spatial orientation of the arch bearing the emitter and the receiver One configuration of the system can be defined as the data from the camera scanning state (for example: normal, horizontal reverse, vertical reverse or horizontal-vertical reverse), the size of the acquisition matrix (for example: 256, 512 or 1024 pixels), the size of the field of view (for example: 11 cm, 16 cm, 22 cm, or 30 cm) and the orientation of the arch in space (given by two angles, for example the anatomical angles).

A reference configuration is defined by fixing the direction of camera scanning (for example normal), the size of the acquisition matrix (for example 512 pixels), the size of the field of view (for example 22 cm) and the orientation of the arch in space (for example, for the frontal plane, the anatomical position corresponding to the frontal position: anatomical angles RAO/LAO=0 and CRA/CAU=0 degrees. For the lateral plane, we preferably take the profile position: anatomical angles RAO/LAO=90 degrees and CRA/CAU=0 degrees).

The distortion field $D_0$ is estimated from an image of the two-dimensional grid phantom acquired in the reference configuration.

By design of the grid phantom, the distortion field is equivalent to the data of the distortion in all the nodes, that is to say a two-dimensional vector giving the offset along the lines and the columns of the image between the node position detected in the grid image and the theoretical position which it would have if the image did not contain any distortion.

A differential distortion field is the difference, node by node, between two distortion fields and is therefore a distortion field itself.

Note that "o" is the application of a distortion field to an image. For example, if I is an image and D a distortion field, the image I'=D o I is the image I distorted by the distortion field D. Similarly, for another field D', the image I"=D' o I' is the image distorted by the distortion field D'. We therefore have I"=D' o D o I=(D' o D) o I. The distortion field D"=D' o D is therefore the distortion field that has to be applied to I to obtain the image I". It can be said that D' is the differential distortion field between the field D and the field D".

It can be assumed that the four causes of variation of distortion (changing, with respect to the reference configuration, the camera scanning, the acquisition matrix, the field of view and/or the orientation of the arch) are independent. Any distortion field D, observed in the images acquired for a particular configuration of the system, comprises the successive application of the reference field $D_O$ then of the differential field due to the change of camera scanning $D_I$, then of the differential field due to changing the acquisition matrix $D_M$, then of the differential field due to the change in the size of the field of view $D_F$, then of the differential field due to the change in the orientation of the arch $D_A$, that is:

$$D = D_A \circ D_F \circ D_M \circ D_I \circ D_o.$$

The method makes it possible to find these differential fields for all the possible configuration of the system.

With regard to the three first causes of variation of distortion (camera reversal, acquisition matrix, field of view), there is a very small number of values that these parameters may take (less than 5 on current systems). Invoking their independence, it is possible to estimate the differential distortion field due to a change in one of them, whatever the value of the other parameters. In particular, it is possible to use the values defined for the reference configuration for the other parameters. For example, for the camera reversal changes, three calibration configurations can be defined as follows:

$I_1$: all the parameters are the same as in the reference configuration, except the camera scanning is horizontally reversed;

$I_2$: all the parameters are the same as in the reference configuration, except the camera scanning is vertically reversed; any $I_3$: all the parameters are the same as in the reference configuration, except the camera scanning is vertically and horizontally reversed.

The distortion fields $D_1$, $D_2$, and $D_3$ are estimated by acquiring a grid image in the configurations $I_1$, $I_2$, and $I_3$ respectively. The differential distortion fields $D_{11}$, $D_{12}$ and $D_{13}$ are then determined by comparing $D_1$, $D_2$ and $D_3$ respectively with $D_0$. The comparison amounts to establishing the differential distortion vector for each node of the grid.

To find the distortion D for a particular configuration, it is enough to observe the state of the camera scanning:

If there is no camera reversal, the distortion $D_1$ will be zero.

If the camera scanning is carried out in horizontal reversal, $D_1 = D_{11}$.

If the camera scanning is carried out in vertical reversal, $D_1 = D_{12}$.

If the camera scanning is carried out in vertical and horizontal reversal, $D_1 = D_{13}$.

A similar procedure is carried out to establish the differential distortion fields corresponding to the changes of acquisition matrix and of field of view size.

The distortion field, even with the camera reversal, the acquisition matrix and the field of view kept constant, will vary if the orientation of the arch is modified. This is due to the fact that the distortion appears in part because the electrons which are created in the brightness amplifier see their path modified by the action of the local electromagnetic field, this modification being dependent on the angle between the direction of the local electromagnetic field and the path of the electrons. If the orientation of the brightness amplifier is modified, the respective angle between the local electromagnetic field and the path of the electrons is also modified and a variation of distortion follows.

Unlike the three first parameters, the orientation of the arch takes continuous values (therefore infinite potential values). It is therefore not possible a priori to estimate a differential distortion field for each orientation: this is done for a finite number of positions, called control positions and from this, the differential field for any other position is deduced as needed, and not during calibration, by biquadratic interpolation.

Figure 1:
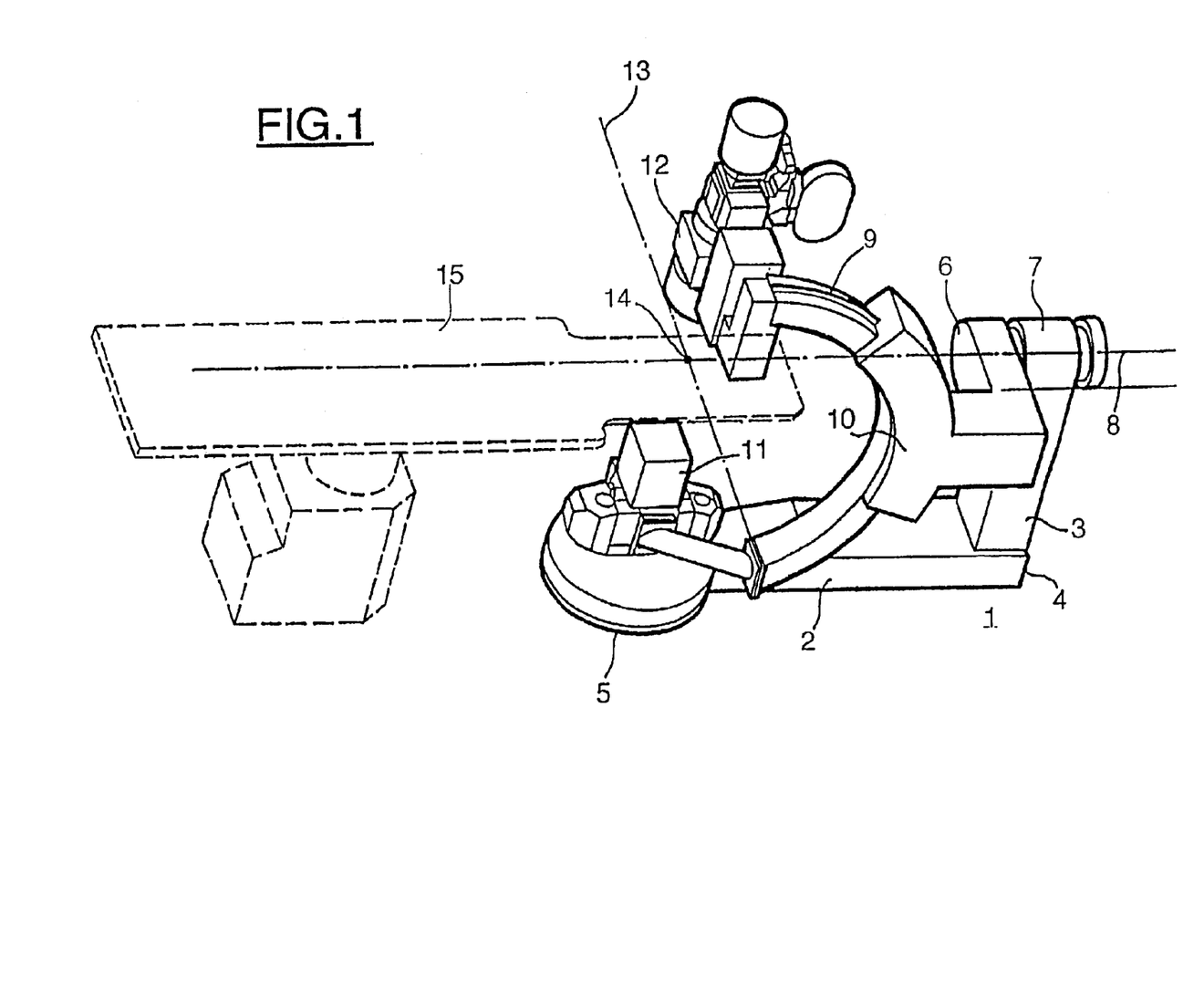
FIG. 1 is a perspective view of a radiology system with three axes which can be used to implement an embodiment of the method.

In FIG. 1, the radiology system comprises an L-shaped stand 1, with a substantially horizontal base 2 and a substantially vertical support 3 attached to an end 4 of the base 2. At the opposite end 5, the base 2 has an axis of rotation parallel to the support 3 and about which the stand is capable of rotating. A support arm 6 is attached by a first end to the top 7 of the support 3, so as to rotate about an axis 8. The support arm 6 may have the shape of a bayonet. A C-shaped circular arm 9 is held by another end 10 of the support arm 6. The C-shaped arm 9 is capable of sliding rotationally about an axis 13 relative to the end 10 of the support arm 6.

The C-shaped arm 9 supports an X-ray tube 11 and a radiation detector 12 in diametrically opposed positions facing each other. The detector 12 has a plane detection surface. The direction of the X-ray beam is determined by a straight line joining a focal point of the tube 11 to the center of the plane surface of the detector 12. The three axes of rotation of the stand 1, of the support arm 6 and of the C-shaped arm 9 are secants at a point 14. In the midposition, these three axes are mutually perpendicular.

A table 15, designed to receive a patient, has a longitudinal orientation aligned with the axis 8 in the rest position.

By way of example, a set of images of a blood vessel is acquired for different positions of the radiology system. A three-dimensional image can then be reconstructed from the set of two-dimensional images. Two-dimensional views of the three-dimensional image can be interactively produced.

Figure 2:
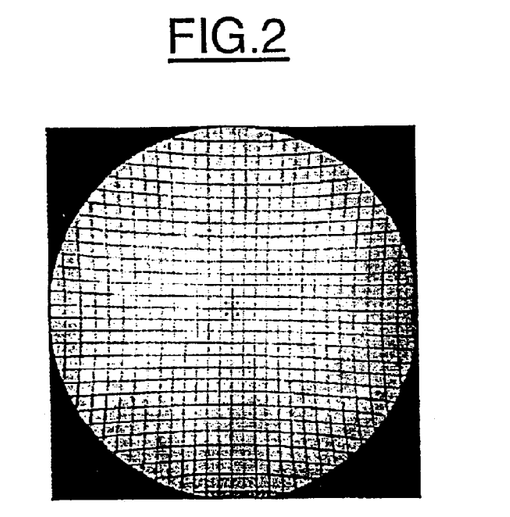
FIG. 2 is a view of a calibration grid as observed on a means for displaying images associated with the radiology system.

FIG. 2 shows an example of an image of a calibration grid as can be observed on a display screens of a radiology system. The grid is arranged in the place of an object to be radiographed in the path of the X-ray beam between the X-ray tube 11 and the X-ray detector 12. The grid has a square mesh made of a material which is opaque or relatively opaque to X-rays, for example lead or copper. Note that the image of the grid is not a faithful reproduction thereof. If the center of the grid is appropriately reproduced, the edges have distortions which it is sought to calculate. At a given point of the grid, the distortion can be characterized by a vector having a direction and a magnitude.

Among the causes of distortion, it is seen that some, such as the detector faults, are independent of the angulations around the axes of the radiology apparatus, while others depend on the angulations. An ideal calibration would require calculating the distortion at every point of the image field, for any angulation along each of the axes, and more generally, for any configuration of the system, which would require enormous calculations resources.

It is sought to obtain a satisfactory calibration relatively quickly and at reasonable cost. A calculation of the distortion field is carried out for a few so-called control angulations from which a distortion field is deduced for the other angulations. In order to simplify the calculations, the spatial position of the tube 11 and of the detector 12 will be considered, not with respect to the axes of rotation of the radiology apparatus, but with respect to two axes, preferably mutually orthogonal and passing through the isocenter, perpendicular to the direction for the X-ray beam, in other words, defining a plane parallel to the axis 13. The third axis of a marker formed from the said two axes is the direction of the X-ray beam. Rotation of the tube 11 and of the detector 12 about this third axis has no effect on the distortion. The angulations with respect to the said two axes are called $\theta$ and $\Phi$.

The taking of images can be modeled geometrically as a conic projection perturbed by a two-dimensional distortion field in the image.

The image detector 12 is sensitive to the surrounding electromagnetic field, which introduces image distortions with respect to the conic projection model. A projection function is therefore seen as a combination of a conic projection and a distortion function, which will both depend on the current state of the apparatus. The distortion is a function of the image plane in itself. The distortion is assumed to be fairly regular. It is then possible to accurately estimate it by calculating it over a number of points scattered in the image, its value at the other points being deduced there from by interpolation.

The phantom used for calibrating the distortions consists of a grid. Each intersection of the grid is called a node. The position of each node is detected in the image. The distortion at each node is defined as the distant between its position in the image and the position that it should have in the ideal model of the grid. When the distortion is corrected, the conic projection hypothesis is applicable. The latter is a homographic function of three-dimensional space in which the object is expressed towards the image plane. It results in estimating a 3×4 matrix to within a multiplicative constant. Thus there are eleven parameters to estimate: five intrinsic parameters modeling the image sequence and six extrinsic parameters giving the respective position of the X-ray emitting-receiving set and of the object imaged in space. The conic projection is estimated by virtue of another phantom consisting of a plastic cylinder transparent to X-rays in which lead balls arranged in a helix are carried. This helix makes it possible to have about thirty visible points in the image. The detection of these points and their matching with those of the perfect model of the helix makes it possible to determine the parameters of the conic projection.

By knowing a priori the configuration of the system in which an image will be taken, it is then possible to determine with considerable accuracy the distortion function by virtue of the grid and the conic projection by virtue of the helix. By approximation, it is considered that the earth's magnetic field is uniform locally and hardly varies in a time interval of around a few days. It is also considered that the earth's magnetic field is even, which makes it possible to consider a small number of samples or control positions, therefore a small number of images of the grid.

For each axis defining the orientation, three, or even four, control angulations prove to be useful. Therefore nine or even sixteen control positions defined by an angulation and an interpolation of the biquadratic or even bicubic type result there from. The angulation in question may be a "machine" angulation with respect to each of the two axes or, preferably, an anatomical angulation with two angles ($\theta$, $\Phi$) different from the "machine" angles, but being able to be expressed as a function there of.

The control positions will be chosen to be evenly spaced and symmetrical with respect to the origin, in order to optimize the density of the positions in the parameter space. For the biquadratic interpolation, a set of positions will therefore be given by positive values $\theta_0$ and $\Phi_0$, which define control points in space ($\theta$, $\Phi$): (0, 0), ($-\theta_0$, 0), ($\theta_0$, 0), (0, $-\Phi_0$), (0, $\Phi_0$), ($-\theta_0$, $-\Phi_0$), ($-\theta_0$, $\Phi_0$), ($\theta_0$, $-\Phi_0$) and ($\theta_0$, $\Phi_0$). A higher number of control points can be provided.

In order to obtain satisfactory accuracy, it is worth avoiding the extrapolation, that is to say generating a distortion value for angulations located outside the interval between $-\theta_0$ and $\theta_0$, $-\Phi_0$ and $\Phi_0$. Therefore the values of $\theta_0$ and $\Phi_0$ corresponding to all or to a large range of all the possible angulations will be chosen so that the set of estimates is carried out by interpolation, $\theta_0$ and $\Phi_0$ remaining less than or equal to 90°.

The principle of quadratic interpolation is as follows. Three so-called control points $P_i=(x_i, y_i)$ in the plane can be connected by a quadratic curve:

$$P(u) = [\,u^2 \quad u \quad 1\,] M \begin{bmatrix} P_0 \\ P_1 \\ P_2 \end{bmatrix}$$

where M is a characteristic matrix of the quadratic interpolation:

$$M = \begin{bmatrix} 2 & -4 & 2 \\ -3 & 4 & -1 \\ 1 & 0 & 1 \end{bmatrix}$$

and u the interpolation parameter of interpolation varying between 0 and 1.

For the biquadratic interpolation, the parameters of a path of a point in the plane are set by two interpolation parameters u and v, and are expressed as follows:

$$P(u, v) = [\,v^2 \quad v \quad 1\,] M \begin{bmatrix} P_{0,0} & P_{0,1} & P_{0,2} \\ P_{1,0} & P_{1,1} & P_{1,2} \\ P_{2,0} & P_{2,1} & P_{2,2} \end{bmatrix} M' \begin{bmatrix} u^2 \\ u \\ 1 \end{bmatrix} \quad (1)$$

where M' is a characteristic matrix of the biquadratic interpolation.

Generalization to a higher number of points is possible. The interpolation function connects the control points at any point of the path by the interpolation parameters u and v. More specifically, these points are connected to anatomical angles defined as a function of systems angles u and v can be taken as reduced coordinates of the anatomical angles of the sort $u=(\theta-\theta_{min})/(\theta_{max}-\theta_{min})$.

However, it is preferable to take $u=f((\theta-\theta_{min})/(\theta_{max}-\theta_{min}))$ and $v=g((\Phi-\Phi_{min})/(\Phi_{max}-\Phi_{min}))$; where f and g are increasing uneven functions, such as f(1)=1 and f'(1)=0, which leads to a polynomial function of type $ax^5+bx^3+cx$.

More specifically, using a function including a constant A, which depends on the type of radiology apparatus and which will be the same for the same series of systems. The distortion function is then written: type $f(x)=\alpha(A+\beta)x^5+\chi(A+\delta)x^3+\epsilon(A+\Phi)x$.

A good approximation is provided by the following function: $f(x)=(A-1.5)x^5+(2.5-2A)x^3+Ax$, where A is between 0 and 15/8. The value of A=1.25 is of particular benefit to the extent that it makes it possible to obtain a suitable estimate of the distortion. By way of example, for a field of 16, the mean error is about 0.8 pixel with 1.95 pixels the maximum error. For a field of 22, the mean error is about 0.75 pixel with a maximum error of 1.65 pixels. For a field of 30, the mean error is about 0.6 pixel with a maximum error of 1.42 pixels.

More general, N control points are defined, hence N orientations $(A_n)_{1 \leq n \leq N}$, each orientation $A_n$ being defined by the coordinate angles $(\theta_n, \Phi_n)$ of the $n^{th}$ control point. N configurations of the system are defined:

the camera scanning is the same as for the reference configuration (for example, normal scanning);

the acquisition matrix is the same as for the reference configuration (for example, matrix 512);

the size of the field of view is the same as for the reference configuration (for example, field of 22 cm);

the orientation is that corresponding to the control point:
$A_n = (\theta_n, \Phi_n)$;

A grid image is acquired for those N configurations, from which N differential distortion fields $(D_{An})_{1 \leq n \leq N}$ are defined by comparing distortion fields observed for the N configurations with the distortion field for the reference configuration.

By interpolation, a differential distortion is found for a configuration identical to the reference configuration, if it is only the orientation that is different. That is $D_A$ is the differential distortion for this configuration. The rectangle formed by the 9 control points for the biquadratic interpolation, or 16 for the bicubic interpolation which surround the point of coordinates is $(\theta, \Phi)$ are determined in orientation space. These 9 (or 16) points are not unique in general, but the continuity properties of the interpolations chosen guarantee that the result does not depend on the set of points retained, since it properly frames the point $(\theta, \Phi)$. Therefore retain 9 (or 16) differential distortion fields.

A differential distortion field is a set of two-dimensional vectors giving the distortion for all the nodes of the grid.

By interpolation, given the current orientation $(\theta, \Phi)$, the value of the differential distortion d is found for each node of the grid. Thus, the differential distortion field $D_A$ is determined for the current orientation $(\theta, \Phi)$.

Figure 3:
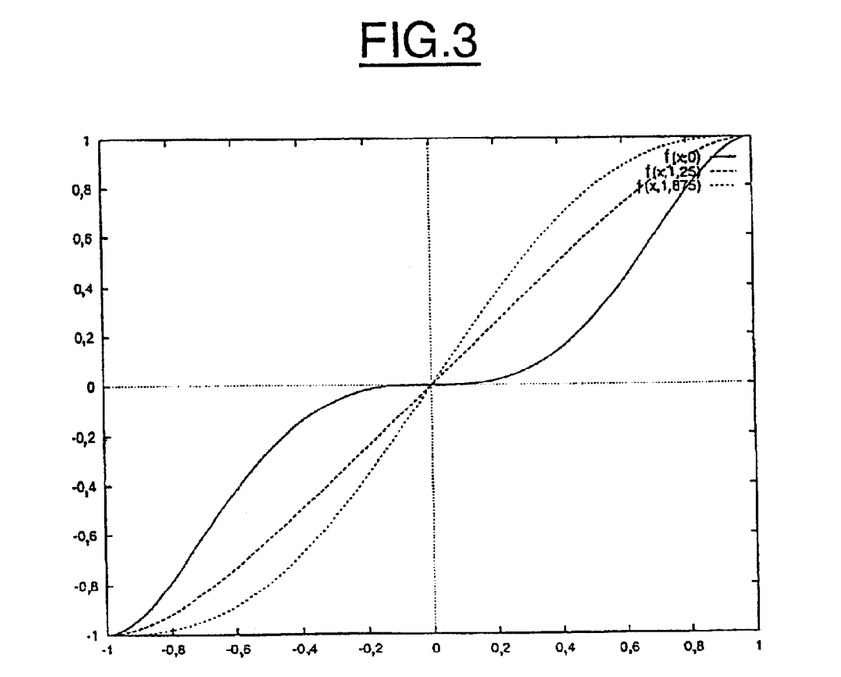
FIG. 3 is a curve of the function u(x) for several parameter settings.

FIG. 3 shows the different shapes taken by the function $f(x, A)$ by varying A between 0 and 1.875.

To complete the estimate of the distortion, it is possible to consider a different interpolation function along each axis, for example by adapting the constant A. The constant A may be subject to automatic estimation depending on the data from a calibration consisting of nine images.

In a particular embodiment of the invention, it is sought to estimate two distortion fields, the field $D_0$ connected to the earth's electromagnetic field at the location of the radiology system and the field $D_V$ connected to the various angulations of the radiology system. It is thus possible to carry out a weekly or monthly calibration of the distortion field $D_0$ because of the relatively fast change of the earth's electromagnetic field and to carry out calibration of the distortion field $D_V$ only at greater intervals, for example every six months or annually because of the slower drift in this distortion.

It is also possible to calculate a reverse distortion field $D_I$ which is connected to a reversal of the image by reversing the video scanning of the detector. This is because, since the detector is not perfect, the reversal of scanning also creates a distortion which it is useful to understand, especially in neuroradiology applications, in particular with dual-plane radiology systems equipped with two tubes and two detectors, for which the mechanical reversal of taking pictures, while moving, for example, the tube from the right to the left and the detector from the left to the right, is not possible. The distortion field $D_I$ is estimated by comparing an image obtained by normal scanning then turned over with an image obtained by reverse scanning of the same grid.

Furthermore, it is possible to improve the estimate of the distortion by taking account of the change of the image field. A distortion field $D_R$ is then estimated connected to adjusting the detector resolution.

Thus, a complete calibration is implemented during reception and star commissioning of the apparatus. Then a partial calibration is implemented at short time intervals and a complete calibration is implemented at long time intervals. The partial calibration may consist only in recalculating the distortion field $D_0$ connected to the earth's electromagnetic field.

Figure 4:
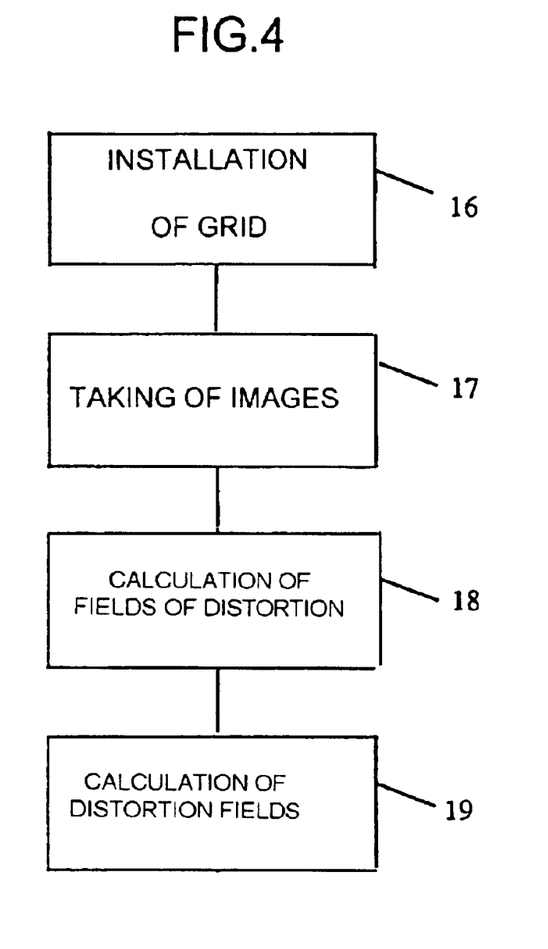
FIG. 4 is a flowchart of the steps of an embodiment of the method.

The complete calibration may include the following steps as shown in FIG. 4:

Step 16: installation of the grid in the path of the high-energy beam by a person responsible for maintenance;

Step 17: the taking nine images of the grid for the control points: $(0, 0)$, $(-\theta_0, 0)$, $(\theta_0, 0)$, $(0, -\Phi_0)$, $(0, \Phi_0)$, $(-\theta_0, -\Phi_0)$, $(-\theta_0, \Phi_0)$, $(\theta_0, -\Phi_0)$ and $(\theta_0, \Phi_0)$;

Step 18: calculation of the fields of distortion corresponding to the control points, and Step 19: calculation of the distortion fields $D_0$ and $D_V$.

Steps 17 and 18 may be carried out partially at the same time in order to reduce the length of time of the complete calibration. The other distortion fields $D_I$ and $D_R$ will be subject to specific steps as required, such as, for the field $D_I$ taking an image of the grid for the control point $(0, 0)$ in reverse scanning, turning over the image of the grid for the control point $(0, 0)$ in normal scanning and comparing, and for the field $D_R$ taking images of the grid for the control point $(0, 0)$ at different resolutions and comparisons.

The partial calibration may comprise the following steps:

a) installation of the grid on the path of the high-energy beam by a person responsible for maintenance;

b) taking of an image of the grid for the control point $(0, 0)$; and c) calculation of the corresponding distortion field $D_0$.

It is then possible to combine the distortion field $D_0$ and the distortion fields $D_V$, $D_I$, $D_R$ and $D_F$ which are not modified during partial calibration in order to obtain the distortion fields interpolated for any angulation $(\theta, \Phi)$ when it is desired to correct an image of the distortion contained therein.

Let us now reconsider the initial problem which consists in estimating the distortion field D for a configuration of the given machine.

The differential distortion field $D_I$ corresponding to the change of camera scanning between the reference configuration and the configuration being studied ("current configuration"), is known.

The differential distortion field $D_M$ corresponding to the change of acquisition matrix between the reference configuration and the current configuration is known.

The differential distortion field $D_F$ corresponding to the change in size of the field of view between the reference configuration and the current configuration, is known.

The differential distortion field $D_A$ corresponding to the change in orientation of the arch between the reference configuration and the current configuration, is known (by interpolation).

Thus, it is possible to deduce there from the distortion field for the current configuration of the system:

$$D = D_A \circ D_F \circ D_M \circ D_I \circ D_0$$

In an embodiment of the invention an economic calibration is available, with shorter immobilization times of the imaging system from the maintenance point of view, and with high accuracy, part of which is carried out during installation of the imaging system and does not have to be implemented subsequently and which is particularly suitable for finding the correspondence of two-dimensional images and three-dimensional images, which makes the three-dimensional reconstructions possible from a limited number of views. It is possible to stop the use of external markers, in radiology, and to benefit from calibration carried out before the arrival of the patient, which reduces the time of the radiological examination carried out on the patient. It is possible to carry out measurements in two-dimensional images with an increased accuracy.

Various modifications in structure and/or steps an/or function may be made by one skilled in the art without departing form the scope and extent of the invention as recited in the claims.

What is claimed is:

1. A method for calibrating an imaging system, having
   (a) means for emitting a high-energy beam;
   (b) means for receiving the high-energy beam after it has passed through a member to be studied;
   (c) means for controlling the receiving means;
   (d) means for supporting the member; and
   (e) means for editing images; comprising:
   (f) calibrating intrinsic parameters relating to the various types of image which can be taken in a predetermined configuration of the system, the intrinsic parameters being estimated using a two-dimensional phantom in order to establish a distortion field for a particular configuration, the distortion field for any configuration being calculated by combining a plurality of distortion fields from causes assumed to be independent.

2. The method according the claim 1 comprising: determining a distortion field $D_o$ due to the earth's electromagnetic Field from an image of the phantom taken in a central position of the imaging system along each axis of rotation, the distortion field $D_o$ being independent of angulation of the system.

3. The method according to claim 2 comprising:
   (a) calibrating for predetermined angular positions of the means for emitting and the means for receiving the intrinsic parameters relating to the various types of image that can be taken;
   (b) the intrinsic parameters being estimated using a two-dimensional phantom in order to establish the distortion field for a particular angulation;
   (c) the distortion field for any angulation being calculated by polynomial interpolation of the distortion fields; and
   (d) each field established for a control point, the control point being defined by a particular angulation for each axis of rotation of the imaging system, having to be subject to calibration.

4. The method according to claim 3, wherein the control point is close to each extreme of angular position.

5. The method according to claim 4, wherein the interpolation function is of the biquadratic or bicubic type.

6. The method according to claim 3, wherein the interpolation function is of the biquadratic or bicubic type.

7. The method according to claim 1 comprising:
   (a) calibrating for predetermined angular positions of the means for emitting and the means for receiving the intrinsic parameters relating to the various types of image that can be taken;
   (b) the intrinsic parameters being estimated using a two-dimensional phantom in order to establish the distortion field for a particular angulation;
   (c) the distortion field for any angulation being calculated by polynomial interpolation of the distortion fields; and
   (d) each field established for a control point, the control point being defined by a particular angulation for each axis of rotation of the imaging system, having to be subject to calibration.

8. The method according to claim 7, wherein the control point is close to each extreme of angular position.

9. The method according to claim 8 wherein the interpolation function is of the biquadratic or bicubic type.

10. The method according to claim 7 wherein the interpolation function is of the biquadratic or bicubic type.

11. The method according to claim 1 comprising: establishing a relationship between interpolation parameters u, v and the angulation, the relationship being of the type $u(x)=ax^5+bx^3+cx$, where x is a coordinate of one point, such that the distortion field is determined as a function of the angulation, the interpolation function determines the distortion as a function of the interpolation parameters u, v.

12. The method according to claim 11, wherein the function $u(x)$ is of the type $u(x)=\alpha(A+\beta)x^5\chi(A+\delta)x^3+\epsilon(A+\Phi)x$, where A is a dependent constant of the type of imaging system, $\alpha$, $\beta$, $\chi$, $\delta$, $\epsilon$ and $\Phi$ being constants which are determined experimentally.

13. The method according to claim 1 comprising: determining a distortion field $D_I$ due to an image reversal by reversing the scanning direction of the means for receiving the high-energy beam by comparing an image of the phantom, which image is turned over after being taken, with an image of the phantom taken with reverse scanning, for the scanning changes used.

14. The method according to claim 1 comprising: determining a distortion field $D_R$ due to a change in resolution of the means for receiving the high-energy beam by comparing an image of the phantom taken at a first resolution with an image of the phantom taken at a second resolution different from the first, for the resolution changes used.

15. The method according to claim 1 comprising: determining a distortion field $D_M$ due to a change of acquisition matrix of the means for receiving the high-energy beam by comparing an image of the phantom taken using a first acquisition matrix with an image of the phantom taken using a second acquisition matrix different from the first, for the changes of acquisition matrix used.

16. A medium for storing instructions to implement a process for calibrating an imaging system comprising:
   (a) means for emitting a high-energy beam;
   (b) means for receiving the high-energy beam after it has passed through a member to be studied;
   (c) means for controlling the receiving means;
   (d) means for supporting the member; and
   (e) means for editing images;
wherein the instructions comprise intrinsic parameters relating to the various types of image which can be taken are calibrated in a predetermined configuration of the system, the intrinsic parameters being estimated using a two-dimensional phantom in order to establish a distortion field for a particular configuration, the distortion field for any configuration being calculated by combining a plurality of distortion fields from causes assumed to be independent.

17. The medium according to claim 16 wherein the instructions comprise determining a distortion field $D_o$ due to the earth's electromagnetic field from an image of the phantom taken in a central position of the imaging system along each axis of rotation, the distortion field $D_o$ being independent of angulation of the system.

18. The medium according to claim 16 wherein the instructions comprise:
   (a) calibrating for predetermined angular positions of the means for emitting and the means for receiving the intrinsic parameters relating to the various types of image that can be taken;
   (b) the intrinsic parameters being estimated using a two-dimensional phantom in order to establish the distortion field for a particular angulation'

(c) the distortion field for any angulation being calculated by polynomial interpolation of the distortion fields; and (d) each field established for a control point, the control point being defined by a particular angulation for each axis of rotation of the imaging system, having to be subject to calibration.

19. The medium according to claim 18 wherein the instructions comprise defining the control point is closest to each extreme of angular position.

20. The medium according to claim 18 wherein the instructions comprise defining the interpolation function as the biquadratic or bicubic type.

21. The medium according to claim 16 wherein the instructions comprise: establishing a relationship between interpolation parameters u, v and the angulation, the relationship being of the type $u(x)=ax^5+bx^3+cx$, where x is a coordinate of one point, such that the distortion field is determined as a function of the angulation, the interpolation function determines the distortion as a function of the interpolation parameters u, v.

22. The medium according to claim 21 wherein: the function $u(x)$ is of the type $u(x)=\alpha(A+\beta)x^5+\chi(A+\delta)x^3+\epsilon(A+\Phi)x$, where A is a dependent constant of the type of imaging system, $\alpha$, $\beta$, $\chi$, $\delta$, $\epsilon$ and $\Phi$ being constants which are determined experimentally.

23. The medium according to claim 16 wherein the instructions comprise: determining a distortion field $D_I$ due to an image reversal by reversing the scanning direction of the means for receiving the high-energy beam by comparing an image of the phantom, which image is turned over after being taken, with an image of the phantom taken with reverse scanning, for the scanning changes used.

24. The medium according to claim 16 wherein the instructions comprise: determining a distortion field $D_R$ due to a change in resolution of the means for receiving the high-energy beam by comparing an image of the phantom taken at a first resolution with an image of the phantom taken at a second resolution different from the first, for the resolution changes used.

25. The medium according to claim 16 wherein the instructions comprise:

determining a distortion field $D_M$ due to a change of acquisition matrix of the means for receiving the high-energy beam by comparing an image of the phantom taken using a first acquisition matrix with an image of the phantom taken using a second acquisition matrix different from the first, for the changes of acquisition matrix used.

26. An imaging system comprising;

(a) means for emitting a high-energy beam;

(b) means for receiving the high-energy beam after it has passed through a member to be studied;

(c) means for controlling and the means for receiving;

(d) means for editing images; and (e) means for calibrating intrinsic parameters relating to the various types of image which can be taken in a predetermined configuration of the system, the intrinsic parameters being estimated using a two-dimensional phantom in order to establish a distortion field for a particular configuration, the distortion field for any configuration being calculated by combining a plurality of distortion fields from causes assumed to be independent.

27. The imaging system according to claim 26 wherein the means for calibration determines a distortion field $D_o$ due to the earth's electromagnetic field from an image of the phantom taken in a central position of the imaging system along each axis of rotation, the distortion field $D_0$ being independent of angulation of the system.

28. The imaging system according to claim 26 wherein the means for calibration (a) calibrates the intrinsic parameters relating to the various types of image that can be taken;

(b) the intrinsic parameters being estimated using a two-dimensional phantom in order to establish the distortion field for a particular angulation;

(c) the distortion field for any angulation being calculated by polynomial interpolation of the distortion fields; and (d) each field established for a control point, the control point being defined by a particular angulation for each axis of rotation of the imaging system, having to be subject to calibration.

29. The imaging system according to claim 28 wherein the control point is close to each extreme of angular position.

30. The imaging system according to claim 28 wherein the interpolation function is of the biquadratic or bicubic type.

31. The imaging system according to claim 26 wherein establishing a relationship between interpolation parameters u, v and the angulation, the relationship being of the type $u(x)=ax^5+bx^3+cx$, where x is a coordinate of one point, such that the distortion field is determined as a function of the angulation, the interpolation function determines the distortion as a function of the interpolation parameters u, v.

32. The imaging system according to claim 31 wherein the function $u(x)$ is of the type $u(x)=\alpha(A+\beta)x^5+\chi(A+\delta)x^3+\epsilon(A+\Phi)x$; where A is a dependent constant of the type of imaging system, $\alpha$, $\beta$, $\chi$, $\delta$, $\epsilon$ and $\Phi$ being constants which are determined experimentally.

33. The imaging systems according to claim 26 wherein determining a distortion field $D_I$ due to an image reversal by reversing the scanning direction of the means for receiving the high-energy beam by comparing an image of the phantom, which image is turned over after being taken, with an image of the phantom taken with reverse scanning, for the scanning changes used.

34. The imaging system according to claim 26 wherein determining a distortion field $D_R$ due to a change in resolution of the means for receiving the high-energy beam by comparing an image of the phantom taken at a first resolution with an image of the phantom taken at a second resolution different from the first, for the resolution changes used.

35. The imaging system according to claim 26 wherein determining a distortion field $D_M$ due to a change of acquisition matrix of the means for receiving the high-energy beam by comparing an image of the phantom taken using a first acquisition matrix with an image of the phantom taken using a second acquisition matrix different from the first, for the changes of acquisition matrix used.

* * * * *